US006331653B1

United States Patent
Matsushita et al.

(10) Patent No.: US 6,331,653 B1
(45) Date of Patent: Dec. 18, 2001

(54) PROCESS FOR PRODUCING 3,4-DIHYDROXY-3-CYCLOBUTENE-1,2-DIONE

(75) Inventors: Shoshiro Matsushita, Tokyo; Ikuo Shimizu; Hiroshi Toyoda, both of Yokkaichi; Asako Tanaka, Matsumoto, all of (JP)

(73) Assignee: Kyowa Yuka Co., Ltd., Tokyo (JP)

( * ) Notice: Subject to any disclaimer, the term of this patent is extended or adjusted under 35 U.S.C. 154(b) by 0 days.

(21) Appl. No.: 09/486,363

(22) PCT Filed: Sep. 7, 1998

(86) PCT No.: PCT/JP98/03989

§ 371 Date: Feb. 28, 2000

§ 102(e) Date: Feb. 28, 2000

(87) PCT Pub. No.: WO99/12881

PCT Pub. Date: Mar. 18, 1999

(30) Foreign Application Priority Data

Sep. 5, 1997 (JP) .................................................. 9-240578

(51) Int. Cl.[7] .................................................. C07C 45/00
(52) U.S. Cl. ............................................ 568/347; 568/348
(58) Field of Search ...................... 568/347, 348

(56) References Cited

U.S. PATENT DOCUMENTS

| | | | |
|---|---|---|---|
| 5,130,492 | 7/1992 | Scholl et al. | 568/348 |
| 5,808,166 | 9/1998 | Shimizu et al. | 568/348 |

FOREIGN PATENT DOCUMENTS

| | | |
|---|---|---|
| 0 442 431 | 11/1991 | (EP) . |
| 0 842 919 | 5/1998 | (EP) . |
| 4-330034 | 11/1992 | (JP) . |
| 97/37961 | 10/1997 | (WO) . |

OTHER PUBLICATIONS

Helvetica Chimica Acta, vol. 61 (5), pp. 1784–1813. (1978).
Izv. Akad. Nauk SSSR, Ser. Khim. (1981), (2), pp. 439–440.

Primary Examiner—Alan Siegel
(74) Attorney, Agent, or Firm—Fitzpatrick, Cella, Harper & Scinto

(57) ABSTRACT

The present invention provides a method for manufacturing 3,4-dihydroxy-3-cyclobutene-1,2-dione represented by the following general formula (III) (usual name: "squaric acid") through the following reaction processes 1~4, using a vinyl ether represented by the following general formula (V) and a halogenoacetyl halide represented by the following general formula (VI) as starting materials.

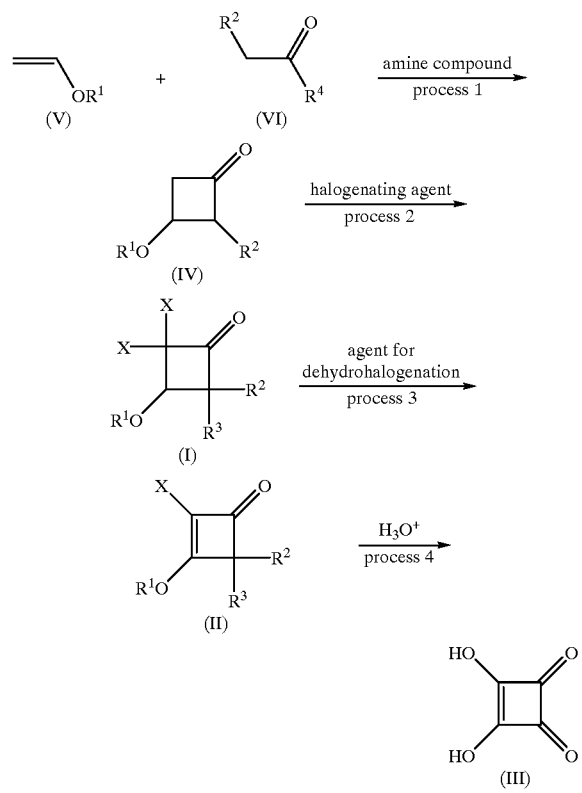

[wherein, $R^1$ represents an alkyl group; and $R^2$, $R^3$, $R^4$, and X are the same or different and each represents halogen]

6 Claims, No Drawings

PROCESS FOR PRODUCING 3,4-DIHYDROXY-3-CYCLOBUTENE-1,2-DIONE

TECHNICAL FIELD

The present invention relates to a method for manufacturing 3,4-dihydroxy-3-cyclobutene-1,2-dione easily and efficiently.

BACKGROUND ART 3,4-Dihydroxy-3-cyclobutene-1,2-dione (usual name: "squaric acid") is known as a useful starting material for pharmaceuticals, in addition to functional materials such as photosensitive materials for electrophotography, medium material for optical discs, optical sensitizers, and the like [Chemical Reviews, 93, 449, (1993); Japanese Patent Application, First Publication Laid Open No. Hei 4-106400; Japanese Patent Application, First Publication Laid Open No. Hei 2-306247; Japanese Patent Application, First Publication Laid Open No. Hei 2-48665; Japanese Patent Application, First Publication Laid Open No. Hei 5-5005; Japanese Patent Application, First Publication Laid Open No. Hei 5-96173; and the like].

Hitherto, several methods for manufacturing 3,4-dihydroxy-3-cyclobutene-1,2-dione are known. However, all known methods have problems such as need for many steps, difficulty in synthesizing starting materials, hard reaction conditions, low yields, requirements for special manufacturing equipment, and the like.

Examples of the known methods include (1) a method using a triketene as a starting material (disclosed in Jackson, B. et. al., EP442431, and the like); (2) a method using 4-hydroxy-3-cyclobutene-1,2-dione as a starting material [disclosed in Bellus, D. et. al., Helv. Chim. Acta, 61, 1784 (1978)]; (3) a method using a tetraalkoxyethylene as a starting material [disclosed in Bellus, D., J. Org. Chem., 44, 1208 (1979)]; (4) a method using a dialkoxyacetylene as a starting material [disclosed in Pericas, M. A., Tetrahedron Letters, 4437 (1977)]; (5) a method using a tetrahalogeno-ethylene as a starting material [disclosed in J. Amer. Chem. Soc., 81, 3480 (1959), and the like]; (6) a method using hexachlorobutadiene as a starting material (disclosed in Hagenberg, P. et. al., Ger. Offen, No. 1568291, and the like); (7) a method using carbon monoxide as a starting material [disclosed in Silvestri, G. et. al., Electrochim. Acta, 23, 413 (1978)]; and the like.

However, each of the aforementioned methods has the following problems. That is, according to the method (1), it is difficult to obtain a large amount of the starting material since a triketene is a side product in the production of a diketene. According to the method (2), the method for acquiring the starting material is a solid culturing method with poor productivity or a synthetic method requiring many steps. The method (3) has a difficulty in synthesizing the starting materials, in addition to a low yield. The method (4) has a difficulty in synthesizing the starting materials. The method (5) has a difficulty in synthesizing the starting materials, in addition to requiring many steps. The method (6) provides a low yield. The method (7) requires special manufacturing equipment.

Further, in Liebigs Ann. Chem., 686, 55 (1965), a method for manufacturing 3,4-dihydroxy-3-cyclobutene-1,2-dione from 1,1,2,3,4,4-hexachloro-1,3-butadiene is disclosed. However, this method provides a low yield of the desired final product.

In addition, in J. Amer. Chem. Soc., 84, 2919 (1962), a method for manufacturing 3,4-dihydroxy-3-cyclobutene-1,2-dione via 2-chloro-3-ethoxy-4,4-difluolo-2-cyclobutene-1-one is disclosed. However, this method has problems such as a low yield in the synthesis of the starting material, 1-chloro-2,4,4-triethoxy-3,3-difluolocyclobutene, and a low yield of the desired final product.

Additionally, a method for manufacturing a 3-alkoxy-2-halogenocyclobutanone derivative, which is used as an intermediate in producing 3,4-dihydroxy-3-cyclobutene-1,2-dione in the present invention, is disclosed in Abramova, N. M. et. al., Izv. Akad. Nauk SSSR, Scr. Khim., 2, 439 (1981). However, the yield of the desired product according to this method is as low as 35%, which is unsatisfactory for a practical use.

The object of the present invention is to provide a method for manufacturing 3,4-dihydroxy-3-cyclobutene-1,2-dione, easily and efficiently.

DISCLOSURE OF THE INVENTION

The present invention provides a method for manufacturing 3,4-dihydroxy-3-cyclobutene-1,2-dione represented by the following general formula (III), characterized in that a 3-alkoxy-2,2,4,4-tetrahalogcenocyclobutanone derivative represented by the following general formula (I) is treated in the presence of an agent for dehydrohalogenation, to yield a 3-alkoxy-2,4,4-trihalogceno-2-cyclobutene-1-one derivative represented by the following general formula (II), and then the 3-alkoxy-2,4,4-trihalogeno-2-cyclobutene-1-one derivative is further hydrolyzed.

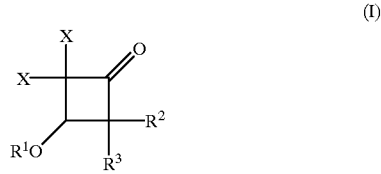

(I)

[wherein, $R^1$ represents an alkyl group; and $R^2$, $R^3$ and X are the same or different and each represents halogen]

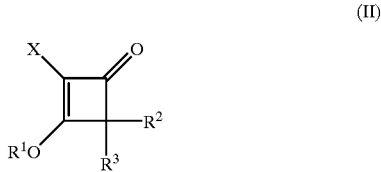

(II)

[wherein, $R^1$, $R^2$, $R^3$ and X have the same meanings as described above]

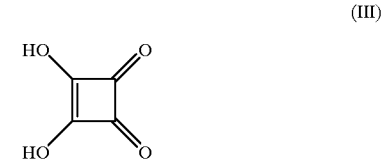

(III)

The 3-alkoxy-2,2,4,4-tetrahalogenocyclobutanone derivative represented by the aforementioned general formula (I) can be obtained by means of reacting a 3-alkoxy-2-halogenocyclobutanone derivative represented by the following general formula (IV) with a halogenating agent.

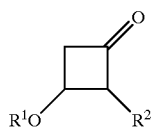

[wherein, $R^1$ and $R^2$ have the same meanings as described above]

Additionally, the 3-alkoxy-2-halogenocyclobutanone derivative represented by the aforementioned general formula (IV) can be obtained by means of reacting a vinyl ether represented by the following general formula (V) with a halogenoacetyl halide represented by the following general formula (VI) in the presence of an amine compound with a pKa value of approximately 6.0~8.0 (in an aqueous solution at 25° C.).

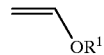

[wherein, $R^1$ represents an alkyl group]

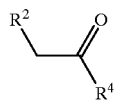

[wherein, $R^2$ and $R^4$ are the same or different and each represents halogen]

In other words, a vinyl ether represented by the aforementioned general formula (V) is reacted with a halogenoacetyl halide represented by the aforementioned general formula (VI) in the presence of an amine compound with a pKa value of approximately 6.0~8.0 (in an aqueous solution at 25° C.), to yield a 3-alkoxy-2-halogenocyclobutanone derivative represented by the aforementioned general formula (IV). The resultant derivative is further reacted with a halogenating agent, to yield a 3-alkoxy-2,2,4,4-tetrahalogenocyclobutanone derivative represented by the aforementioned general formula (I). The resultant derivative is treated in the presence of an agent for dehydrohalogenation to yield a 3-alkoxy-2,4,4-trihalogeno-2-cyclobutene-1-one derivative represented by the aforementioned general formula (II), and then the 3-alkoxy-2,4,4-trihalogeno-2-cyclobutene-1-one derivative is further hydrolyzed to yield 3,4-dihydroxy-3-cyclobutene-1,2-dione represented by the aforementioned general formula (III).

Furthermore, at least one compound selected from the group consisting of N-methylmorpholine, N-ethylmorpholine, N,N-diethylaniline, and 2,4,6-trimethylpyridine is preferably used as the aforementioned amine compound with a pKa value of approximately 6.0~8.0 (in an aqueous solution at 25° C.).

BEST MODES OF CARRYING OUT THE INVENTION

In the definition of each group of the aforementioned general formulae (I), (II), (IV), (V), and (VI), the alkyl group represents a straight- or branched-chain alkyl group having 1~18 carbons, examples of which may include a methyl group, ethyl group, propyl group, isopropyl group, butyl group, isobutyl group, sec-butyl group, tert-butyl group, pentyl group, isoamyl group, neopentyl group, 2-pentyl group, 3-pentyl group, hexyl group, heptyl group, octyl group, 2-ethylhexyl group, nonyl group, decyl group, dodecyl group, pentadecyl group, octadecyl group, and the like. The halogen represents an atom of fluorine, chlorine, bromine, iodine, or the like.

In the following, the manufacturing method of the present invention is described.

The compound represented by the general formula (III) (hereinafter, referred to as the compound (III); the compounds represented by the other general formula numbers are also referred to in a similar manner) can be obtained according to the following reaction processes.

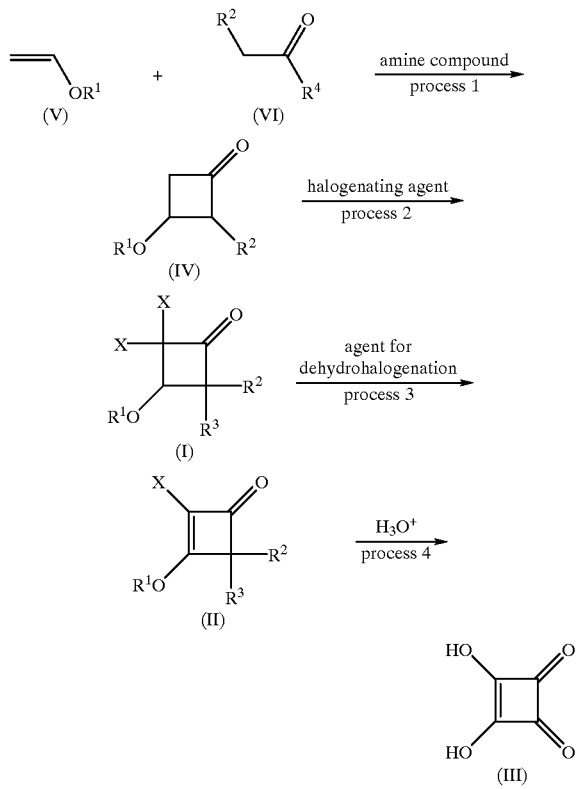

[wherein, $R^1$, $R^2$, $R^3$, $R^4$, and X have the same meanings as described above]

In the following, the aforementioned processes 1 through 4 are each described in detail.

Process 1: Manufacturing of compound (IV) (3-alkoxy-2-halogenocyclobutanone derivative)

The starting materials for the aforementioned, i.e., the compound (V) (a vinyl ether) and compound (VI) (a halogenoacetyl halide) are available as commercial products.

Initially, an amine compound is added in a dropwise manner, in a 0.8~1.2, preferably 1.0~1.2 equivalent amount of that of the compound (VI), to the mixture comprising the compound (VI); the compound (V), in a 0.8~2, preferably 1~1.5 equivalent amount of that of the compound (VI); and a reaction solvent, followed by a reaction which yields the compound (IV). The amine compound used therein possesses a pKa value of approximately 6.0~8.0 (in an aqueous solution at 25° C.), and may be diluted, if necessary, with a solvent which is identical to or different from the aforementioned reaction solvent. Additionally, if necessary, after the dropwise addition of the amine compound, the resultant compound may be aged.

Examples of the aforementioned compound (VI), i.e., the halogenoacetyl halide, may include fluoroacetyl fluoride, fluoroacetyl chloride, fluoroacetyl bromide, fluoroacetyl iodide, chloroacetyl fluoride, chloroacetyl chloride, chloroacetyl bromide, chloroacetyl iodide, bromoacetyl fluoride, bromoacetyl chloride, bromoacetyl bromide, bromoacetyl iodide, iodoacetyl fluoride, iodoacetyl chloride, iodoacetyl bromide, iodoacetyl iodide, and the like.

Examples of the aforementioned compound (V), i.e., the alkyl vinyl ether, may include methyl vinyl ether, ethyl vinyl ether, propyl vinyl ether, isopropyl vinyl ether, n-butyl vinyl ether, isobutyl vinyl ether, sec-butyl vinyl ether, tert-butyl vinyl ether, pentyl vinyl ether, isoamyl vinyl ether, neopentyl vinyl ether, 2-pentyl vinyl ether, 3-pentyl vinyl ether, hexyl vinyl ether, octyl vinyl ether, 2-ethylhexyl vinyl ether, nonyl vinyl ether, decyl vinyl ether, dodecyl vinyl ether, pentadecyl vinyl ether, octadecyl vinyl ether, and the like.

In addition, preferred examples of the aforementioned amine compound with a pKa value of approximately 6.0~8.0 (in an aqueous solution at 25° C.) may include N-methylmorpholine, N-ethylmorpholine, N,N-diethylaniline, 2,4,6-trimethylpyridine, and the like. These compounds may be used alone or in combinations of two or more.

The aforementioned reaction solvent may comprise any solvent that is inert to the reaction, examples of which may include ethers such as diethyl ether, diisopropyl ether, tetrahydrofuran, 1,4-dioxane, tert-butyl methyl ether, and the like; halogenated hydrocarbons such as chloroform, dichloromethane, 1,2-dichloroethane, and the like; aromatic hydrocarbons such as benzene, toluene, xylene, and the like; N, N-dimethylformamide; N,N-dimethylacetoamide; and dimethylsulfoxide. These solvents may be used alone or in combinations of two or more.

The reaction in the process 1 is performed generally at a temperature in the range of 0~100° C., preferably 30~70° C. Additionally, aging is performed at a temperature in the range of 0~100° C. for 30 minutes to 5 hours.

Further, the compound (IV) obtained in the reaction is produced as four types of diastereomer compounds (VII) and (VIII) represented by the following general formulae (VII) and (VIII), respectively.

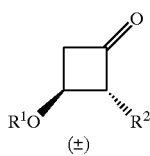

(VII)

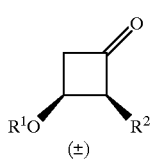

(VIII)

[wherein, $R^1$ and $R^2$ have the same meanings as described above]

Either of these diastereomer compounds (VII) and (VIII) may be used as the starting material in the following process 2. Additionally, the compound (VIII) may be converted to the compound (VII) quantitatively, by means of heating or treatment with an amine compound.

Process 2: Manufacturing of compound (I) (3-alkoxy-2,2,4,4-tetrahalogeno-cyclobutanone derivative)

The compound (IV) is reacted with a halogenating agent in a 3~6, preferably 3~4 equivalent amount of that of the compound (IV), if necessary in the presence of a basic compound, in a 3~6, preferably 3~4 equivalent amount of that of the compound (IV), or a phosphorous compound in a 1~3 equivalent amount of that of the compound (IV), with or without a reaction solvent, to yield the compound (I), via agining, if necessary. The reaction proceeds in a similar manner regardless of whether the starting material, compound (IV), is either one of the aforementioned two diastereomers, or a mixture thereof.

Examples of the aforementioned halogenating agent may include chlorine, bromine, iodine, phosphorus pentachloride, sulfuryl chloride, N-bromosuccinimide, N-chlorosuccinimide, and the like.

Examples of the aforementioned basic compound may include organic basic compounds such as pyridine, triethylamine, quinoline, and the like; inorganic basic compounds such as sodium hydroxide, potassium hydroxide, sodium carbonate, potassium carbonate, sodium bicarbonate, and the like; and basic organic acid salts such as sodium acetate, potassium acetate, and the like. These basic compounds may be used alone or in combinations of two or more.

Examples of the aforementioned phosphorus compound may include phosphorus tribromide, phosphorus trichloride, and the like.

The aforementioned phosphorus compound and basic compound may be used in combination.

The reaction solvent used in the process 2 may be any solvent which is inert to the reaction, examples of which may include the same reaction solvents which are described in process 1, and water. These reaction solvents may be used alone or in combinations of two or more.

The temperature at the time of adding the halogenating agent in the process 2 is in the range of 0~100° C., preferably 0~50° C. Aging is performed at a temperature in the range of 0~100° C. for 10 minutes to 3 hours.

Process 3: Manufacturing of compound (II) (3-alkoxy-2,4,4-trihalogeno-2-cyclobutene-1-one derivative)

The compound (I) is treated with an agent for dehydrohalogenation, with or without a reaction solvent, to yield the compound (II).

The reaction solvent used in the process 3 can be any solvent which is inert in the reaction, examples of which may include alcohols including methanol, ethanol, propanol, isopropanol, and the like; aliphatic hydrocarbons such as hexane, heptane, octane, isooctane, cyclohexane, and the like; ketones such as acetone, methyl ethyl ketone, methyl isobutyl ketone, diisopropyl ketone, diethyl ketone, and the like; esters such as ethyl acetate, methyl acetate, and the like; in addition to the aforementioned solvents described in the process 1. These reaction solvents may be used alone or in combinations of two or more.

Examples of the aforementioned agent for dehydrohalogenation may include organic basic compounds such as triethylamine, tributylamine, pyridine, quinoline, and the like; inorganic or organic lithium salts such as lithium chloride, lithium bromide, lithium iodide, lithium acetate, lithium carbonate, and the like; and polar amide compounds such as N,N-dimethylformamide, N,N-dimethylacetamide, and the like. These agents for dehydrohalogenation may be used alone or in combinations of two or more. The usage amount of the agent for dehydrohalogcenation is preferably at least 0.5 equivalent amount of that of the compound (I), more preferably at least 0.8 equivalent amount of that of the compound (I).

The reaction in the process 3 is performed at a temperature in the range of room temperature to 120° C. for 30 minutes to 12 hours.

Process 4: Manufacturing of compound (III) (3,4-dihydroxy-3-cyclobutene-1,2-dione)

In the process 4, the compound (II) is hydrolyzed to yield the compound (III) by means of heating with an aqueous acidic solution, with or without a reaction solvent.

The reaction solvent in the process 4 can be any solvent which is inert to the reaction, examples of which may include alcohols such as methanol, ethanol, propanol, isopropanol, and the like; and acetic acid; in addition to the aforementioned solvents described in the process 1. These reaction solvents may be used alone or in combinations of two or more.

Examples of the aforementioned aqueous acidic solution may include an aqueous sulfuric acid solution; an aqueous hydrogen chloride solution; an aqueous acetic acid solution; an aqueous nitric acid solution; an aqueous phosphoric acid solution; and the like; and mixtures thereof. The concentration of the aqueous acidic solution is 1~90% by weight, preferably 10~60% by weight. The usage amount of the aqueous acidic solution is not particularly limited, however, it is preferably used in an amount such that the amount of the acid is at least one molar amount of that of the compound (II).

The reaction temperature in the process is in the range of 80~120° C., preferably 90~110° C., and the reaction time is preferably in the range of 1~48 hours.

The intermediates obtained in the aforementioned processes 1 through 4, (i.e., the compounds (I), (II), and (IV)) and the desired compound (i.e., the compound (III)) can be isolated and purified according to an ordinary purification method used in the synthetic organic chemistry such as distillation, filtration, extraction, washing, drying, concentration, recrystallization, various types of chromatography, or the like. Additionally, the intermediates can be used for the next reactions without being purified.

Further, the compounds (I), (II), (III) and (IV) may exist in the form of addition products with water or various types of solvents, which are also included in the concept of the present invention.

EXAMPLES

In the following, examples of the present invention are described. However, the present invention is not limited to these examples.

Example 1

Synthesis of 2-chloro-3-isobutoxycyclobutanone (compound (IV)) (Process 1)

A solution formed by dissolving 30.0 g of isobutyl vinyl ether (0.3 mol) as the compound (V) and 34.9 g of chloroacetyl chloride (0.3 mol) as the compound (VI) in 135 ml of tert-butyl methyl ether was heated to 50~55° C. with stirring. Subsequently, a solution formed by dissolving 30.3 g of N-methylmorpholine (with a pKa value of 7.4) (0.3 mol) in 45 ml of tert-butyl methyl ether was added dropwise to the aforementioned solution over two hours. Four hours after the completion of the dropwise addition, 40 ml of water was added thereto in order to separate the solution, followed by removal of the water layer. Analysis of the organic layer using gas chromatography under the following analysis conditions, revealed a yield of 75.8% for the compound (IV), 2-chloro-3-isobutoxycyclobutanone. Furthermore, after concentration of the aforementioned organic layer, a sample for analysis was obtained by means of distillation, and analyzed by means of elemental analysis and nuclear magnetic resonance analysis (NMR).

(Conditions for gas chromatography analysis)

Also in the following examples and comparative examples, samples were analyzed under the same conditions. Column: TC-17 (manufactured by GL Science) comprising 0.25 mm (inner diameter)×30 m (length) Temperature: After maintaining a temperature of 50° C. for 0.5 min, the temperature was raised by 10° C. per minute, and kept at 240° C. for 4 minutes. Carrier gas: Nitrogen gas Detector: FID (Flame Ionization Detector)

Elemental analysis value: (Composition formula $C_8H_{13}O_2Cl$)

|  | H | C |
| --- | --- | --- |
| Calculated value (%) | 7.42 | 54.40 |
| Found value (%) | 7.45 | 53.44 |

Boiling point: 61~64° C./1.6~1.7 mmHg
NMR analysis value:
$^1$H-NMR (CDCl$_3$): δ(ppm) 0.94 (3H, dd, J=1.0, 6.6 Hz), 0.96 (3H, dd, J=1.0, 6.6 Hz), 1.92 (1H, septet, J=6.6 Hz), 3.13 (1H, ddd, J=3.7, 6.6, 18.0 Hz), 3.28 (1H, ddd, J=2.2, 7.8, 18.0 Hz), 3.33 (1H, dd, J=6.6, 9.0 Hz), 3.41 (1H, dd, J=6.6, 9.0 Hz), 4.17 (1H, ddd, J=5.1, 6.6, 7.8 Hz), 4.79 (1H, ddd, J=2.2, 3.7, 5.1 Hz) $^{13}$C-NMR (CDCl$_3$): δ(ppm) 19.2, 28.4, 49.4, 66.7, 73.4, 77.3, 196.9 NMR analysis value for the isomer (diastereomer, corresponding to the compound (VIII))
$^1$H-NMR (CDCl$_3$): δ(ppm) 0.93 (3H, dd, J=2.3, 6.6 Hz), 0.95 (3H, dd, J=2.3, 6.6 Hz), 1.93 (1H, septet, J=6.6 Hz), 3.06 (1H, ddd, J=1.9, 3.6, 17.8 Hz), 3.31 (1H, ddd, J=4.5, 6.6, 17.8 Hz), 3.41 (1H, dd, J=6.6, 8.8 Hz), 3.48 (1H, dd, J=6.6, 8.8 Hz), 4.37 (1H, dt, J=3.2, 6.6 Hz), 4.87 (1H, ddd, J=1.9, 4.5, 6.6 Hz)

Examples 2,3,4, and Comparative Examples 1~8

The reactions were performed in the same manner as in Example 1, with the equivalent mol of the amine compound shown in the following Table 1 instead of 30.3 g of N-methylmorpholine (0.3 mol). After each respective reaction, the yield of 2-chloro-3-isobutoxycyclobutanone was analyzed using gas chromatography. The results are shown below in Table 1.

TABLE 1

| Example | Comparative Example | Amine compound | pKa value | Yield of the compound (IV) (%) |
| --- | --- | --- | --- | --- |
| 1 |  | N-methylmorpholine | 7.4 | 75.8 |
| 2 |  | N-ethylmorpholine | 7.7 | 69.1 |
| 3 |  | 2,4,6-trimethylpyridine | 7.4 | 65.9 |
| 4 |  | N,N-diethylaniline | 6.6 | 43.0 |
|  | 1 | triethylamine | 10.8 | 19.0 |
|  | 2 | N-methylpyrrolidine | 10.5 | 14.0 |
|  | 3 | N-methylpiperidine | 10.1 | 25.2 |
|  | 4 | tributylamine | 9.9 | 4.7 |
|  | 5 | α-picoline | 5.9 | 7.8 |
|  | 6 | Pyridine | 5.2 | 0.5 |
|  | 7 | N,N-dimethylaniline | 5.2 | 18.7 |
|  | 8 | Quinoline | 4.8 | 7.9 |

Example 5

Synthesis of 2,2,4,4-tetrachloro-3-isobutoxycyclobutanone (compound (I)) (Process 2)

Chlorine gas 672 ml was bubbled over 45 minutes into a mixture comprising 1.8 g of 2-chloro-3- isobutoxycyclobutanone (the compound (IV)), 6.2 g of a 20% by weight aqueous sodium acetate solution, and 1.2 g of pyridine, which was kept at a temperature of 20° C. or below 20° C. After the completion of the bubbling of the chlorine gas, the temperature of the reaction solution was raised to 40~50° C., and the solution was aged for two hours. Subsequently, the solution was cooled to room temperature, 2 ml of 10% by weight sodium thiosulfate and 10 ml of dichloromethane were added thereto, and the mixture was stirred, to separate the solution. The organic layer was analyzed using gas chromatography, revealing a 92.5% yield for the compound (I), 2,2,4,4-tetrachloro-3-isobutoxycyclobutanone. After concentration of the aforementioned organic layer, a sample for analysis was obtained by means of distillation. The analysis results are shown in the following.

Elemental analysis value: (Composition formula $C_8H_{10}O_2Cl_4$)

|  | H | C |
| --- | --- | --- |
| Calculated value (%) | 3.60 | 34.32 |
| Found value (%) | 3.64 | 34.23 |

Boiling point: 50~60° C./30 ~40 mmHg
NMR analysis value:
$^1$H-NMR (CDCl$_3$): δ(ppm) 1.03 (6H, d, J=6.6), 2.08 (1H, quintet, J=6.6), 3.64 (2H,d, J=6.6), 4.64 (1H, s)
$^{13}$C-NMR (CDCl$_3$): δ(ppm) 19.1, 28.7, 79.2, 84.3, 90.3, 184.3

Example 6

Synthesis of 2,4,4-trichloro-3-isobutoxy-2-cyclobutene-1-one (compound (II)) (Process 3)

A solution formed by dissolving 5.0 g of 2,2,4,4-tetrachloro-3-isobutoxycyclobutanone (compound (I)) and 3.6 g of triethylamine in 50 ml of tert-butyl methyl ether was refluxed for four hours. After cooling to room temperature, the solution was washed using 50 ml of 1 mol/L hydrochloric acid, and the organic layer was concentrated. The concentrated residues were separated by means of silica gel column chromatography (the composition of the developing solvent: n-hexane / ethyl acetate=100/1), to yield 3.3 g of the compound (II), 2,4,4-trichloro-3-isobutoxy-2-cyclobutene-1-one (yield=77%).

Example 7

Synthesis of 3,4-dihydroxy-3-cyclobutene-1,2-dione (compound (III)) (Process 4)

2,4,4-Trichloro-3-isobutoxy-2-cyclobutene-1-one (compound (II))(2.54 g) was added to a mixed solution comprising 3.89 g of a 33% by weight aqueous sulfuric acid solution and 8 g of isopropanol, and the resultant solution was refluxed for six hours. After the volatile content was evaporated under heating condition at atmospheric pressure, 1.0 g of 3,4-dihydroxy-3-cyclobutene-1,2-dione (the compound (III)) was obtained by means of collecting the precipitate by filtration (yield=88%).

Example 8

Synthesis of 3,4-dihydroxy-3-cyclobutene-1,2-dione (compound (III)) from isobutyl vinyl ether (compound (V)) and chloroacetyl chloride (compound (VI))

A solution formed by dissolving 360.6 g of isobutyl vinyl ether (the compound (V)) (3.6 mol) and 271.3 g of chloroacetyl chloride (the compound (VI)) (2.4 mol) in 1080 ml of tert-butyl methyl ether was heated to 40~45° C. with stirring. Subsequently, a solution formed by dissolving 242.8 g of N-methylmorpholine (2.4 mol) in 360 ml of tert-butyl methyl ether was dropwise added thereto over two hours. One hour after the completion of the dropwise addition, 300 ml of a 5% aqueous sodium bicarbonate solution was added thereto to separate the solution, and the water layer was removed. The volatile content including tert-butyl methyl ether was removed from the resultant organic layer under reduced pressure. 133.7 Litter of chlorine gas was bubbled at 5° C. over 7.5 hours into the mixture of the obtained residues, 1387.5 g of a 20% by weight aqueous sodium acetate solution, and 267.6 g of pyridine. After the completion of the bubbling of the chlorine gas, the temperature of the reaction solution was raised to 20~25° C., and the solution was aged for one hour. Subsequently, 1 litter of toluene and 400 ml of 10% by weight sodium thiosulfate were added, to separate the solution, and the organic layer was washed using 200 ml of 6% by weight hydrochloric acid to further separate the solution. 483 ml of N,N-dimethylformamide and 73.3 g of lithium chloride were added to the obtained organic layer, and the resultant organic layer was heated to 80~100° C. for 3.5 hours. After the completion of the reaction, the resultant mixture was cooled, 1934 g of a 40% by weight aqueous sulfuric acid solution was added thereto, and the mixture was heated to 80~100° C. for 5.5 hours. After the completion of the reaction, the mixture was cooled to 10° C., and filtrated to yield 166.2 g of 3,4-dihydroxy-3-cyclobutene-1,2-dione (the compound (III)).

INDUSTRIAL APPLICABILITY

The manufacturing method of the present invention is suitable for industrial production, and characterized in that it is possible to obtain the starting materials easily, that it is possible to use conventional synthesis equipment, in addition to a small number of steps, moderate reaction conditions, and providing the desired product efficiently. Accordingly, the present invention provides an effective method for manufacturing 3,4-dihydroxy-3-cyclobutene-1, 2-dione (usual name: "squaric acid") that is useful as a starting material for pharmaceutical products, in addition to functional materials such as photosensitive materials for electrophotography, memory materials for additional storage types of optical discs, optical sensitizers, and the like.

What is claimed is:
1. A method for manufacturing 3,4-dihydroxy-3-cyclobutene-1,2-dione represented by the following general formula (III), characterized in that a 3-alkoxy-2,2,4,4-tetrahalogenocyclobutanone derivative represented by the following general formula (I) is treated in the presence of an agent for dehydrohalogenation, to yield a 3-alkoxy-2,4,4-trihalogeno-2-cyclobutene-1-one derivative represented by the following general formula (II), and then the 3-alkoxy-2,4,4-trihalogeno-2-cyclobutene-1-one derivative is further hydrolyzed

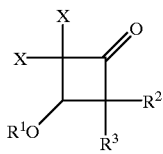
(I)

[wherein, $R^1$ represents an alkyl group; and $R^2$, $R^3$ and X are the same or different and each represents halogen]

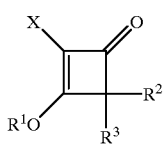
(II)

[wherein, $R^1$, $R^2$, $R^3$ and X have the same meanings as described above]

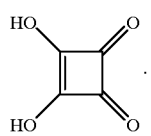
(III)

2. A method for manufacturing a 3-alkoxy-2,2,4,4-tetrahalogenocyclobutanone derivative represented by the following general formula (I), characterized in that a 3-alkoxy-2-halogenocyclobutanone derivative represented by the following general formula (IV) is reacted with a halogenating agent

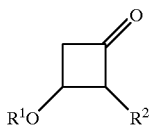
(IV)

[wherein, $R^1$ represents an alkyl group; and $R^2$ represents halogen]

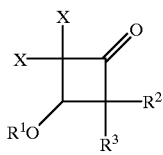
(I)

[wherein, $R^1$ represents an alkyl group; and $R^2$, $R^3$ and X are the same or different and each represents halogen].

3. A method for manufacturing a 3-alkoxy-2-halogenocyclobutanone derivative represented by the following general formula (IV), characterized in that a vinyl ether represented by the following general formula (V) are reacted with a halogenoacetyl halide represented by the following general formula (VI) in the presence of an amine compound with a pKa value of 6.0~8.0 (in an aqueous solution at 25° C.)

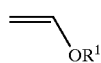
(V)

[wherein, $R^1$ represents an alkyl group]

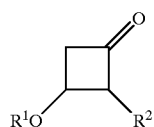
(VI)

[wherein, $R^2$ and $R^4$ are the same or different and each represents halogen]

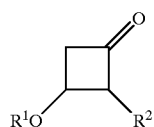
(IV)

[wherein, $R^1$ and $R^2$ have the same meanings as described above].

4. The method for manufacturing a 3-alkoxy-2-halogenocyclobutanone derivative according to the claim 3, wherein said amine compound with a pKa value of 6.0~8.0 (in an aqueous solution at 25° C.) is at least one compound selected from the group consisting of N-methylmorpholine, N-ethylmorpholine, N,N-diethylaniline, and 2,4,6-trimethylpyridine.

5. A method for manufacturing 3,4-dihydroxy-3-cyclobutene-1,2-dione represented by the general formula (III), characterized in that a vinyl ether represented by the following general formula (V) are reacted with a halogenoacetyl halide represented by the following general formula (VI) in the presence of an amine compound with a pKa value of 6.0~8.0 (in aqueous solution at 25° C.), to yield a 3-alkoxy-2-halogenocyclobutanone derivative represented by the following general formula (IV); the resultant derivative is, further reacted with a halogenating agent, to yield a 3-alkoxy-2,2,4,4-tetrahalogenocyclobutanone derivative represented by the following general formula (I); and the resultant derivative is further treated in the presence of an agent for dehydrohalogenation to yield a 3-alkoxy-2,4,4-trihalogeno-2-cyclobutene-1-one derivative represented by the following general formula (II), and then the 3-alkoxy-2,4,4-trihalogeno-2-cyclobutene-1-one derivative is further hydrolyzed to yield 3,4-dihydroxy-3-cyclobutene-1,2-dione represented by the following general formula (III)

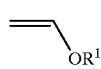
(V)

[wherein, $R^1$ represents an alkyl group]

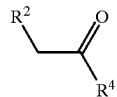

[wherein, $R^2$ and $R^4$ are the same or different and each represents halogen]

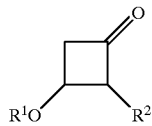

[wherein, $R^1$ and $R^2$ have the same meanings as described above]

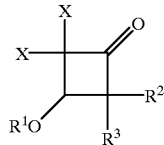

[wherein, $R^1$ represents an alkyl group; and $R^2$, $R^3$ and X are the same or different and each represents halogen]

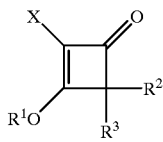

[wherein, $R^1$, $R^2$, $R^3$ and X have the same meanings as described above]

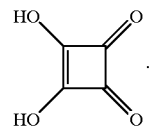

6. The method for manufacturing 3,4-dihydroxy-3-cyclobutene-1,2-dione according to claim 5, wherein said amine compound with a pKa value of 6.0~8.0 (in an aqueous solution at 25° C.) is at least one compound selected from the group consisting of N-methylmorpholine, N-ethylmorpholine, N,N-diethylaniline, and 2,4,6-trimethylpyridine.

* * * * *

UNITED STATES PATENT AND TRADEMARK OFFICE
CERTIFICATE OF CORRECTION

PATENT NO. : 6,331,653 B1
DATED : December 18, 2001
INVENTOR(S) : Shoshiro Matsushita et al.

It is certified that error appears in the above-identified patent and that said Letters Patent is hereby corrected as shown below:

Column 2,
Line 1, "4,4-diflulo-2-" should read -- 4,4-difluoro-2- --;
Line 4, "3,3-difluolocyclobutene," should read -- 3,3-difluorocyclobutene, --.

Column 7,
Line 27, "process" should read -- process 4 --.

Column 10,
Line 11, "133.7 Litter" should read -- 133.7 liter --;
Line 18, "1 litter" should read -- 1 liter --.

Column 11,
Line 63, "are" should read -- is --.

Column 12,
Line 45, "are" should read -- is --;
Line 51, "is," should read -- is --.

Signed and Sealed this

Twenty-seventh Day of May, 2003

JAMES E. ROGAN
*Director of the United States Patent and Trademark Office*